US008496584B2

(12) United States Patent
Tucci

(10) Patent No.: US 8,496,584 B2
(45) Date of Patent: Jul. 30, 2013

(54) MACHINE FOR RAPID IDENTIFICATION OF INFECTIONS AND/OR RISK SITUATIONS RELATED TO GASTRODUODENAL PATHOLOGIES

(75) Inventor: Antonio Tucci, Lesina (IT)

(73) Assignee: Antonio Tucci, Lesina (IT)

( * ) Notice: Subject to any disclaimer, the term of this patent is extended or adjusted under 35 U.S.C. 154(b) by 0 days.

(21) Appl. No.: 12/805,312

(22) Filed: Jul. 26, 2010

(65) Prior Publication Data

US 2010/0292612 A1 Nov. 18, 2010

Related U.S. Application Data

(62) Division of application No. 10/544,840, filed on Aug. 8, 2005, now abandoned.

(51) Int. Cl.
*A61B 5/00* (2006.01)
*A61B 1/00* (2006.01)
*B65D 81/00* (2006.01)

(52) U.S. Cl.
USPC ............................ 600/301; 600/101; 600/584

(58) Field of Classification Search
USPC ................. 600/309, 350, 361, 573, 581, 584, 600/101, 300, 301; 422/68.1, 81
See application file for complete search history.

(56) References Cited

U.S. PATENT DOCUMENTS

| | | | |
|---|---|---|---|
| 3,981,594 A * | 9/1976 | George | 356/246 |
| 4,109,505 A | 8/1978 | Clark et al. | |
| 4,304,488 A * | 12/1981 | Asakura et al. | 356/39 |
| 4,532,936 A * | 8/1985 | LeVeen et al. | 600/575 |
| 4,773,430 A * | 9/1988 | Porath | 600/581 |
| 5,022,382 A * | 6/1991 | Ohshoji et al. | 600/156 |
| 5,158,868 A | 10/1992 | Bergkuist et al. | |
| 5,343,863 A * | 9/1994 | Wiener et al. | 600/437 |

(Continued)

FOREIGN PATENT DOCUMENTS

DE 12 61 279 B 2/1968
WO WO 03032834 A1 4/2003

OTHER PUBLICATIONS

Farinati et al. Abstract of "Perendoscopic gastric pH determination . . . " Aug. 1987. Gastrointestinal Endoscopy. vol. 33 (4). pp. 293-297.

(Continued)

*Primary Examiner* — Max Hindenburg
*Assistant Examiner* — John Pani
(74) *Attorney, Agent, or Firm* — Modiano & Associati; Daniel J. O'Byrne; Albert Josif

(57) ABSTRACT

A machine for performing a method for immediate identification and rapid comparative assessment of indicators of the presence of infections and/or risk situations related to gastroduodenal pathologies, characterized in that it comprises a measurement unit that is constituted by a container supplied by means for aspirating gastric juices in which an agitator of the mixture of gastric juice, reagents and water operates, and at least one probe for sensing the values of the analysis, a hydraulic section that comprises a set of tanks for the reagents required for the analysis and for the water, which are connected to respective apparatuses for feeding said measurement unit and to a pump for feeding water into the stomach of the patient, an apparatus for controlling the temperature of said container, and an electrical section, which comprises a programmable control unit for actuating and controlling said feeder apparatuses and said measurement unit and is suitable to determine the test execution methods.

9 Claims, 5 Drawing Sheets

U.S. PATENT DOCUMENTS

| | | | |
|---|---|---|---|
| 5,477,854 A | | 12/1995 | Essen-Moller |
| 5,507,289 A | * | 4/1996 | Essen-Moller ............... 600/348 |
| 5,902,253 A | | 5/1999 | Pfeiffer et al. |
| 5,989,840 A | | 11/1999 | D'Angelo et al. |
| 6,134,462 A | * | 10/2000 | Rantala ......................... 600/353 |
| 6,241,688 B1 | | 6/2001 | Dvorak et al. |
| 2001/0027269 A1 | * | 10/2001 | Tanaka ......................... 600/368 |

OTHER PUBLICATIONS

Hach Company "SensION Ammonia Gas Sensing Combination Electrode, Model 51927-00". Instruction Manual. 2001.

Watt, PCH. et al. "Relationship between histology and gastric juice pH and nitrite in the stomach after operation for duodenal ulcer." 1984. Gut, vol. 25, pp. 246-252.

Leandro, G. et al. Abstract of [Intragastric pH determination as a screening test in the diagnosis of chronic atrophic gastritis]. Sep. 1989. Minerva Med., 801(9). pp. 1.

Yang, Dae Hyun, et al. "Gastric juice ammonia vs CLO test for diagnosis of *Helicobacter pylori*. . ." May 1995. Digestive Diseases and Sciences, vol. 50, No. 5, pp. 1083-1086.

* cited by examiner

MACHINE FOR RAPID IDENTIFICATION OF INFECTIONS AND/OR RISK SITUATIONS RELATED TO GASTRODUODENAL PATHOLOGIES

This is a divisional of the U.S. application Ser. No. 10/544,840 filed on Aug. 8, 2005 now abandoned.

The present invention relates to a method for rapid identification of infections and/or risk situations related to gastroduodenal pathologies and to a machine for performing the method.

BACKGROUND OF THE INVENTION

It is known that esophagogastroduodenoscopy is currently the main diagnostic technique for pathologies of the upper digestive tract: it also allows to obtain biopsy specimens for possible complementary tests.

While providing excellent macroscopic visualization of the explored viscera, endoscopy alone does not achieve a satisfactory diagnostic sensitivity, since several pathologies do not produce macroscopically detectable changes in the affected organs.

Pathologies frequently associated with normal endoscopic findings are infection with *Helicobacter pylori* (*H. pylori*) and fundal atrophic gastritis. Both conditions are important from the clinical and pathological standpoint: the former (*H. pylori* infection) because in addition to being widespread in the general population (20-90%) it is involved in determining the pathogenesis of many gastroduodenal disorders (ulcer, gastritis, lymphoma, et cetera), and the latter (atrophic gastritis) because it is a neoplastic risk factor.

In order to increase diagnostic possibilities, endoscopy is usually complemented by complementary tests performed on biopsy samples taken during endoscopy. These tests are usually the urease test and histological examination.

Actually, performing these tests does not provide full protection against possible diagnostic errors or omissions. The spot distribution of these pathologies can in fact cause falsely negative results due to the fact that the biopsy samples were taken in areas not affected by the disease. Moreover, falsely positive results are also possible.

The problem worsens if one considers that a substantial percentage of patients subjected to endoscopy is found to have neither *H. pylori* infection nor histological evidence of simple or atrophic gastritis. For these patients, performing the complementary tests leads to an unnecessary increase of the duration of the test (and therefore to greater invasiveness), to consumption of materials (biopsy forceps, test tubes, et cetera) and most of all to a considerable financial expenditure.

The problem could be solved if one could, in some way, predict atrophy and *H. pylori*-status in individuals with normal endoscopic findings. In this manner, complementary diagnostic tests would be performed only in patients who are potentially affected by these pathologies and would be avoided in the others. Such a prediction might also allow a better and more suitable biopsy screening program (with many biopsy samples in the areas most at risk), so as to greatly contain the problem of lesion focality.

SUMMARY OF THE INVENTION

The aim of the present invention is to obviate the cited drawbacks and meet the mentioned requirements, by providing a method that can be performed with an electromedical machine connected to an ordinary endoscopic apparatus, which allows to determine the *H. pylori*-status and detect any fundal atrophic gastritis.

Within this aim, an object of the present invention is to provide a method that is simple, relatively easy to provide in practice, safe in use, effective in operation, and has a relatively low cost.

This aim and this and other objects that will become better apparent hereinafter are achieved with the present method for immediate identification and rapid comparative assessment of indicators of the presence of infections and/or risk situations related to gastroduodenal pathologies, characterized in that it comprises the steps of: during an endoscopic test, aspirating a preset quantity of gastric juices; sending at least part of said aspirated gastric juices to a control unit, where it is subjected to at least one analysis, the outcome of which is provided before said endoscopic test ends.

This method is performed by means of a machine that is characterized in that it comprises a measurement unit that is constituted by a container that is fed by a gastric juice suction pump in which an agitator for agitating the mixture of gastric juice, reagents and water operates, and at least one probe for detecting the values of the analyses, a hydraulic section that comprises a set of tanks for the reagents required for the analyses and for the water, which are connected to respective feed pumps of said measurement unit and to a pump for sending water into the stomach of the patient, a generator of heating air at a low temperature that is connected to said container, and an electrical section, which comprises a programmable control unit for operating and controlling said pumps and said measurement unit, which is suitable to determine the times and methods of execution of the analyses.

BRIEF DESCRIPTION OF THE DRAWINGS

Further characteristics and advantages of the present invention will become better apparent from the following detailed description of a preferred but not exclusive embodiment of a method for rapid identification of infections and/or risk situations related to gastroduodenal pathologies and of the machine for performing the method according to the invention, illustrated by way of non-limiting example in the accompanying drawings, wherein.

DESCRIPTION OF THE PREFERRED EMBODIMENTS

In one aspect the invention regards:

1. A method for immediate identification and rapid comparative assessment of indicators of the presence of infections and/or risk situations related to gastroduodenal pathologies, comprising the steps of: during an endoscopic test, aspirating a preset quantity of gastric juices and sending at least part of said aspirated gastric juices to a control unit, where it is subjected to at least one analysis, the outcome of which is provided before said endoscopic test ends.

2. The method according to paragraph 1, wherein said analysis identifies the presence of *Helicobacter pylori*.

3. The method according to paragraph 2, wherein said analysis determines the concentration of ammonium.

4. The method according to paragraph 3, wherein said analysis is a measurement of the quantity of ammonia that is present and is preceded by the addition of an ISA solution to the gastric juices to convert the ammonium into ammonia.

5. The method according to paragraph 1, wherein said analysis identifies fundal atrophic gastritis.

6. The method according to paragraph 5, wherein said analysis is a measurement of the pH of gastric juice.

In another aspect the present invention regards a machine for performing the method of the present invention for immediate identification and rapid comparative assessment of indicators of the presence of infections and/or risk situations related to gastroduodenal pathologies.

The machine M according to the invention is arranged between an endoscopy unit, designated by U, and a vessel R for collecting the aspirated liquids; in practice, the suction duct of the endoscopy unit U is connected to the inlet of the machine M and the outlet thereof is connected to the collection vessel R (which in turn is connected to the suction unit).

The machine M can be divided schematically into four sections: a measurement unit A, a hydraulic section B, an electrical section C, and a constant-temperature air generator D.

Figure 1:
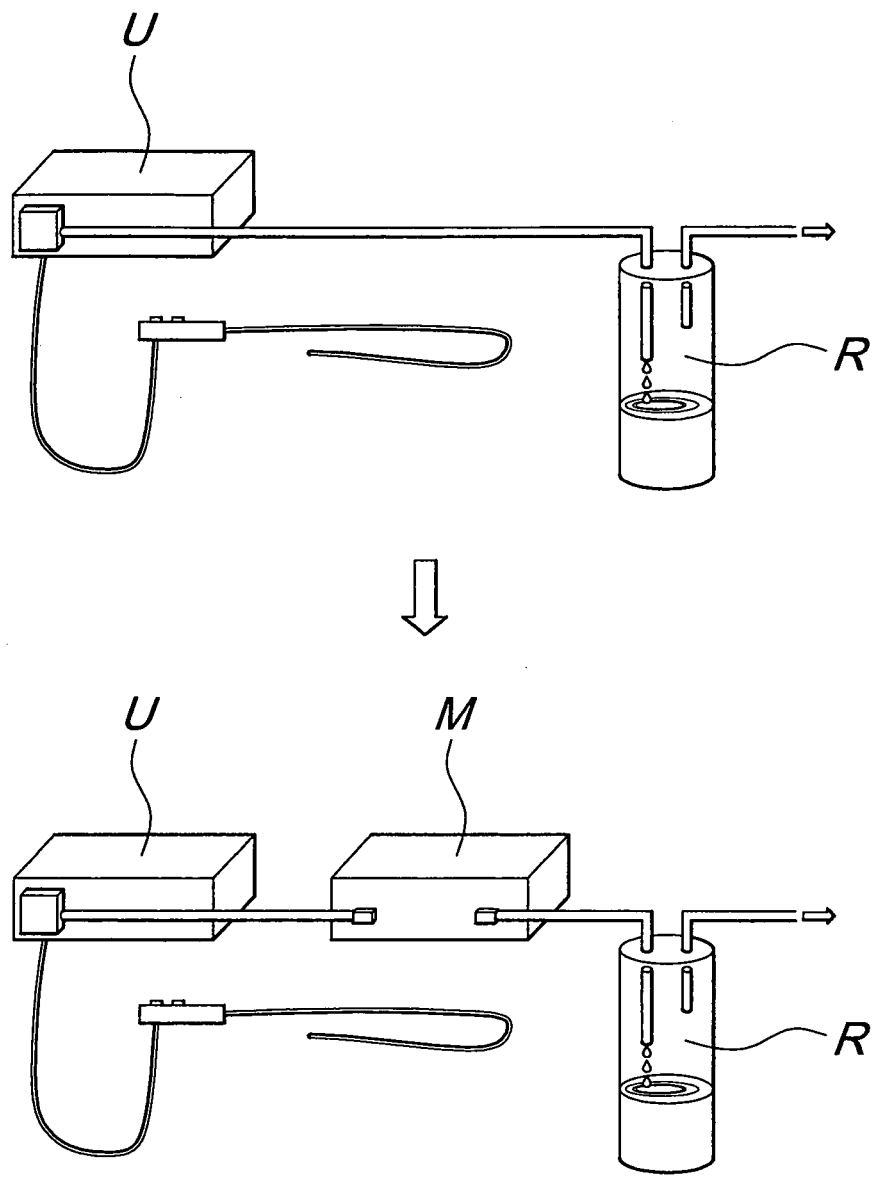
FIG. 1 is an installation diagram of a machine that performs the method according to the invention with respect to the endoscopic unit and to the vessel for collecting the aspirated material.
Figure 2:
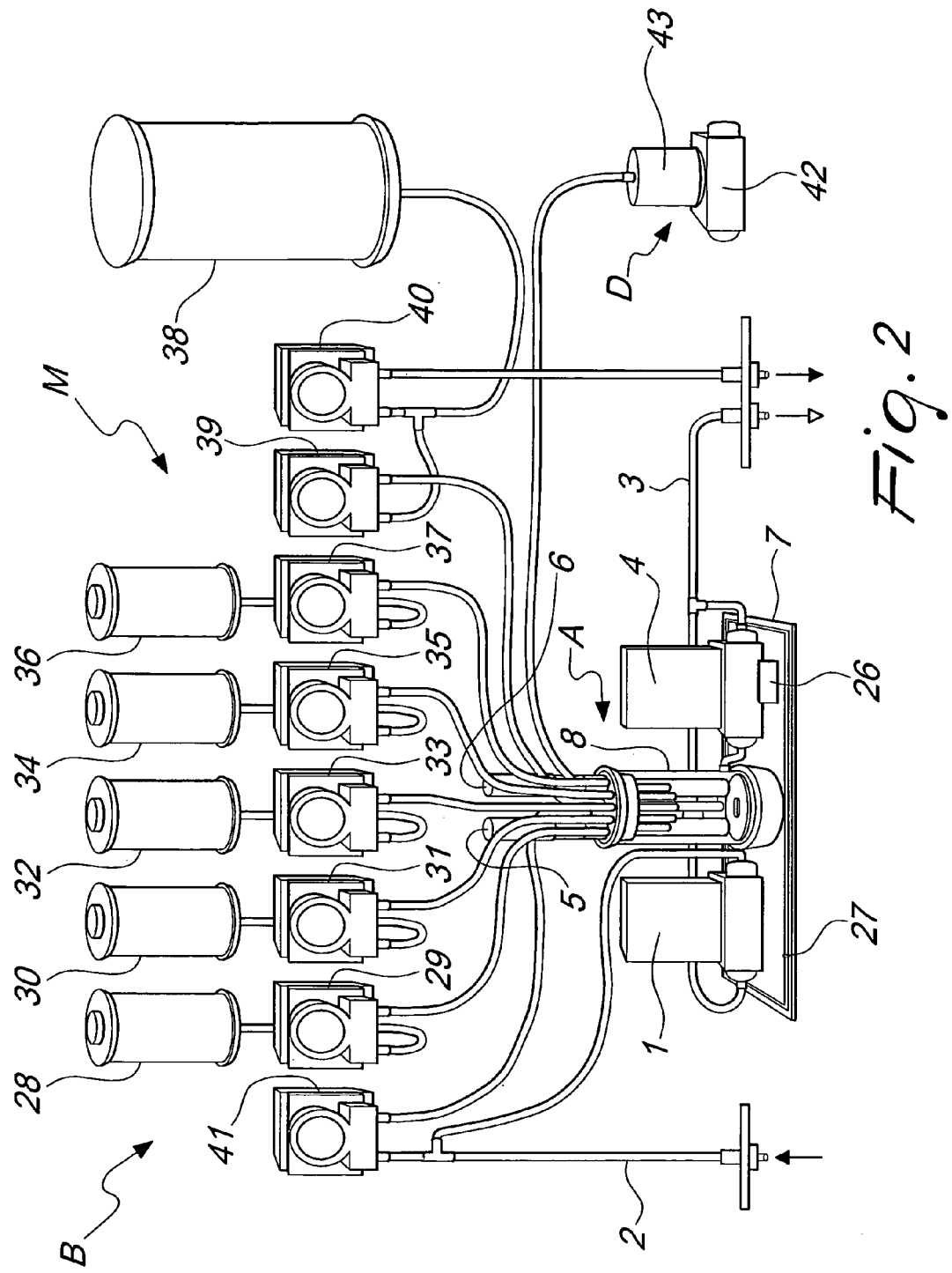
FIG. 2 is a schematic view of a possible embodiment of the machine that performs the method according to the invention.
Figure 3:
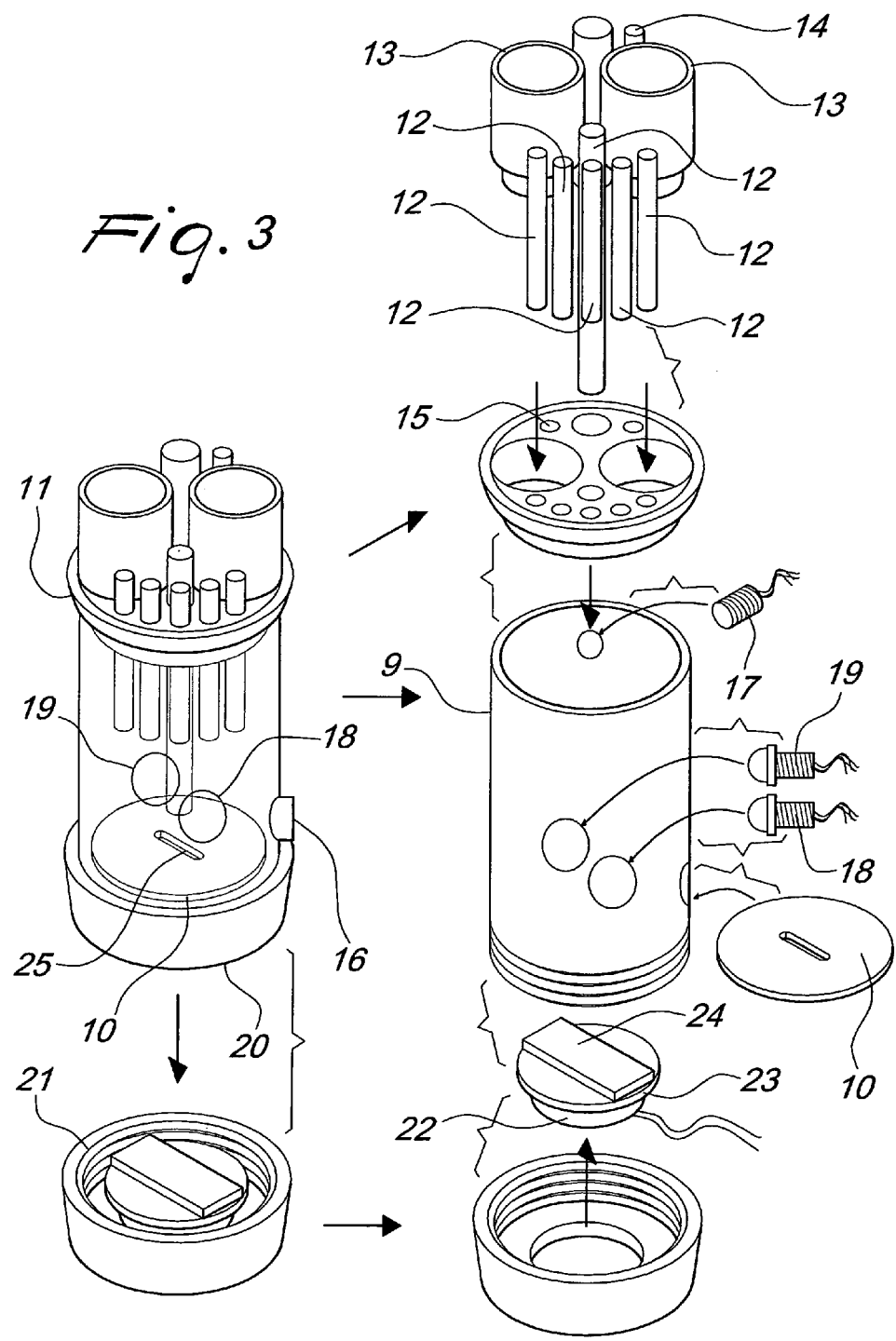
FIG. 3 is an exploded view of the container in which the process for analysis of the gastric juices occurs.

FIG. 2 illustrates the measurement unit A; the hydraulic section B and the constant-temperature air pump D. The measurement unit A consists of a normally-open two-way electric valve 1, which blocks (when activated) the suction on a line 2 for the intake of the gastric juice on the part of a general suction duct 3; a second normally-closed two-way electric valve 4, which allows (when activated) to empty a measurement container 8, a pH measurement probe 5, an ammonia measurement probe 6 (the probe is an ammonia measurement probe; ammonium is measured indirectly by converting it into ammonia (gas) by adding ISA), a supporting panel 7 and a measurement container 8 inside which (measurement chamber) the analysis of the gastric juice occurs. This container, as shown in the exploded view of FIG. 3, is constituted by a cylinder 9 that is advantageously made of a material such as plexiglass, which is closed at its lower end by a thin disk 10 of a material such as polyvinyl chloride, referenced hereinafter with the abbreviation PVC, and at its upper end by a plug 11, also made of PVC, which is crossed by seven ducts for introducing liquids 12, two supporting guides 13 for the probes 5 and 6, a duct 14 for introducing air at a constant temperature of 30-35° C. (depending on the type of probes used), and a venting hole 15. At the intersection between the bottom and the side wall of the container there is an emptying hole 16, which is connected to the suction system (which is not shown and is located downstream of the vessel R); just below the upper plug 11, in an internal point of the cylinder 9, there is instead a temperature sensor 17. At the level that corresponds to the internal volumes of 5 ml and 10 ml there are two electronic level sensors 18 and 19. The supporting base of the container 8 is constituted by a small PVC cylinder 20, inside which there is a receptacle for an agitator 21. The agitator 21 is constituted by a small DC motor 22, on the rotating shaft of which a base 23 is mounted; said base supports a permanently magnetized bar 24, the rotation of which is transmitted, by magnetic coupling, to an armature 25 (also permanently magnetized), which rests above the bottom 10 of the container 8.

All the components of the measurement unit A are fixed to an upper face of the supporting panel 7, which in addition to providing mechanical support also provides (by means of an electric circuit with conducting tracks formed on the surface of the panel 7) the connections between the various electrical components of the unit A and a connector 26 for connection to the electrical section C; an alarm sensor 27 also acts on the panel 7, is suitable to detect and indicate the presence of liquids on the panel 7, and is constituted by two parallel and closely spaced conducting tracks.

The hydraulic section B is substantially constituted by six tanks for liquids, eight peristaltic pumps and a network of ducts that connects the hydraulic section to the measurement unit and to the pneumatic-hydraulic input and output connectors of the machine. Each tank is connected to a specific pump: a tank 28 for the max pH buffer solution is connected to a pump 29, a tank 30 for the max NH4 calibration solution is connected to a pump 31, a tank 32 for the min NH4 calibration solution is connected to a pump 33, a tank 34 for the ISA (ionic strength adaptation) solution is connected to a pump 35, a tank 36 for the min pH buffer solution is connected to a pump 37, and a water tank 38 is connected to two pumps 39 and 40: the first of these two pumps, i.e., the pump 39, is designed to feed water into the measurement container 8, and the second pump 40 is instead designed to pump water into the endoscope U (in order to wash mucous regions covered by mucus, blood or clots, ingested material, et cetera) or into the echoendoscope (for filling the viscera to be explored). The reference numeral 41 designates a pump that introduces the gastric juice in the measurement container 8.

The constant-temperature air generator D is designed to maintain a substantially constant temperature inside the measurement container 8. The generator D consists of an actual air pump 42, which produces a low-pressure air stream, a controlled heating unit 43, which warms (30-35° C.) the generated air, and a temperature sensor 17, which is arranged inside the measurement container 8 and constantly informs the heating unit 43 regarding the temperature inside the measurement container 8.

Figure 4:
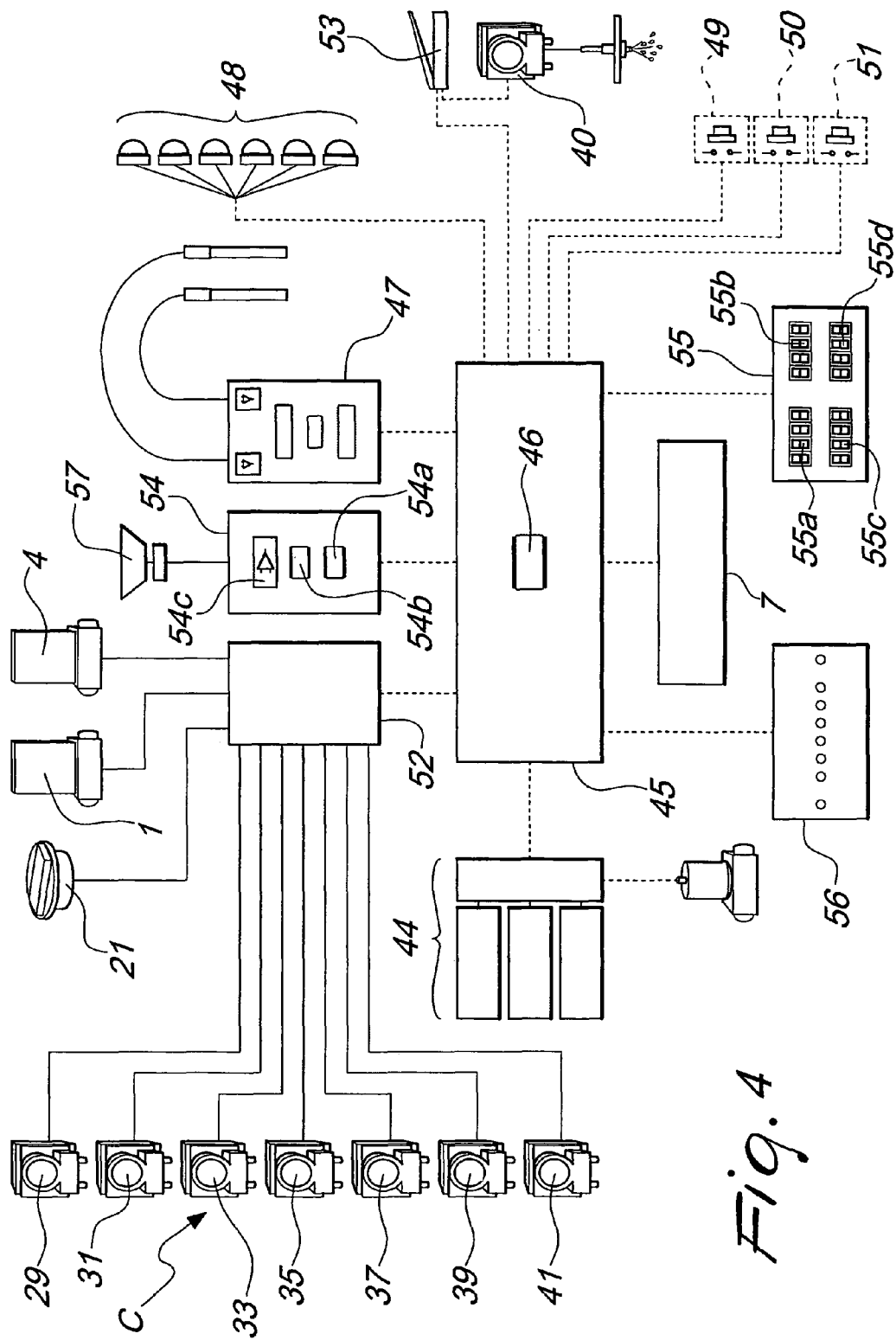
FIG. 4 is a diagram of the electrical and electronic connections of the units assigned to the management, control and user interface of the machine that performs the method according to the invention.

The electrical section C is summarized schematically in FIG. 4 and consists of a power supply unit 44 that supplies current to the entire section C. The various power supply lines are guided on a motherboard 45 and distributed from there to the various user devices. The motherboard 45 is the core of the entire section C; by way of suitable multipolar connectors, it is connected to electrical boards and to the various electromechanical devices (agitator 21, electric valves 1 and 4, pumps 29, 31, 33, 35, 37, 39, 40 and 41) and manages all the functions of the machine M by means of a microprocessor 46. By way of a probe interface board 47, the motherboard 45 receives the information acquired by the probes related to pH and $NH_3$ concentration sensing. The signals emitted by the probes are processed by the board 47 and are sent to the microprocessor 46 of the motherboard 45. From the measurement unit supporting panel 7, the motherboard 45 instead receives the indications related to the movement of the liquids inside the measurement container 8 (detected by the level sensors 18 and 19), and is informed, by way of six further level sensors 48, regarding the filling status of the liquid tanks (28, 30, 32, 34, 36 and 38). The only information it receives from the human operator is: power-on of the machine M (by means of the power-on button 49), start of test (by means of the start button 50), and power-off of the machine M (by means of the power-off button 51). The activation of the electromechanical devices (agitator 21, electric valves 1 and 4, pumps 29, 31, 33, 35, 37, 39, 40 and 41) is managed by means of a driver board 52; all the electromechanical devices are controlled by the microprocessor 46, except for the pump 40, which is activated directly by a pedal 53 that is controlled by the operator. A sound card 54, a display card 55 and a card with luminous indicators 56 are instead used by the machine M to communicate with the outside world. The sound card 54 is provided with a voice synthesis chip 54a on which the messages are prerecorded digitally, an electronic integrated-circuit device 54b, which acts as an intermediary between the microprocessor 46 and the voice synthesis chip, and an amplifier 54c, which is connected to a loudspeaker 57. The display card 55 comprises two display devices 55c and 55d (7-segment bands), on which the microprocessor 46 shows the value of the pH and the value of the ammonium (in ppm), and two millivoltmeters 55a and 55b, which display continuously the operating conditions (signal sent to the microprocessor 46) of the pH measurement probe 5 and of the ammonium concentration measurement probe 6. The card with luminous indicators 56 instead comprises a system of eight two-color light-emitting diodes (known by the acronym LED), which informs the operator regarding the filling condition of the liquid tanks (28, 30, 32, 34, 36 and 38), the suitability for operation of the probes 5 and 6, and the operational status of the machine M.

Figure 5:
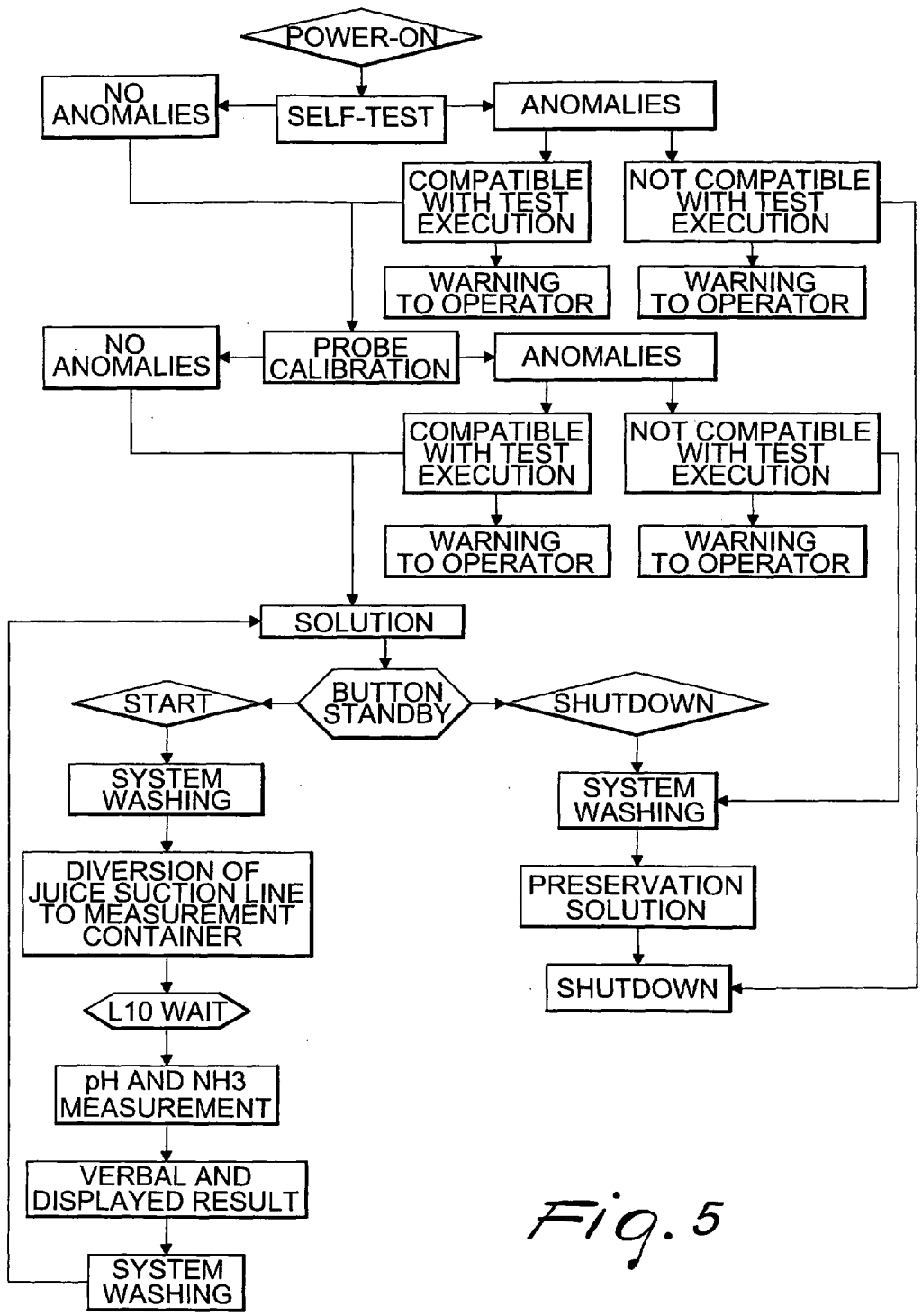
FIG. 5 is a functional block diagram of the machine that performs the method according to the invention.

FIG. 5 illustrates the block diagram of the operation of the device. After power-on (by means of the button 49), the microprocessor 46 performs a self-test to check that the electromechanical devices (agitator 21, electric valves 1 and 4, pumps 29, 31, 33, 35, 37, 39, 40 and 41) are suitable for operation, to check the level of the liquids in the various tanks (28, 30, 32, 34, 36 and 38), and to detect any abnormal losses of liquids inside the machine M. If there are anomalies that are incompatible with correct execution of the tests, or if any loss of liquids is detected, the machine M reports verbally the faulty component or reports the loss of liquids and shuts down automatically. If instead the levels in the tanks (28, 30, 32, 34, 36 and 38) are found to be nearly empty, the machine M reports this shortage verbally to the operator, switches (from green to red) the LED that corresponds to the nearly empty tank on the display card 56, and continues the sequence; in this case, the detected anomaly is in fact compatible with the regular operation of the machine M.

After the self-test, the microprocessor 46 empties (by activating the electric valve 4) and washes with water (deactivation of the electric valve 4 and activation of the water pump 39) the measurement container 8, using the level sensors 18 and 19 as a reference for the movement of the liquids inside the container 8. The microprocessor then calibrates the probes 5 and 6 by introducing sequentially therein the max and min pH buffer solutions (for pH calibration) and the min and max NH4Cl solutions (for ammonium calibration), separating the various steps with a washing cycle and activating the agitator 21 at each measurement. Ammonium measurement is performed after converting said ammonium into ammonia by means of the ISA (ionic strength adaptation) solution, which is added every time ammonium is to be measured; the function of the ISA solution is to increase the pH of the solution to be measured, so as to facilitate the conversion of ammonium into ammonia (gas), which can accordingly be detected by the ammonia probe 6. The resulting ammonium and pH calibration values are compared with reference parameters (suggested by the probe manufacturer); if the operation of the probes 5 and 6 is found to be normal, the values are stored by the microprocessor 46, which will then use them in calculating the measurements of the samples; if the comparison instead shows that one or both probes are not operating correctly, the device reports the anomaly to the operator, specifying that further operations are not possible (on penalty of inaccurate measurements), washes the measurement container 8, introduces the preservation solution therein and shuts down automatically. If instead the resulting values indicate an initial alteration of the probe or probes 5 and 6, the machine M warns the operator of the drop in the performance of the probe or probes 5 and 6, switches (from green to red) the corresponding LED on the display card 56, stores the values and continues the sequence.

After calibration, the microprocessor 46 again washes the measurement container 8 and introduces the solution, whose composition is related to the type of pH and ammonium probe used. The microprocessor then enters a standby condition (warning the operator of its "ready" condition) and cyclically monitors the start button 50 and the power-off button 51.

The testing procedure begins when the operator presses the start button 50 (a few seconds before beginning the gastroscopy). When the button is pressed, the microprocessor 46 produces the suction of the solution and a cycle for washing the container 8; then it activates the electric valve 1 and the pump 41, so that the aspirated material (gastric juice) is diverted into the measurement container. At this point, the operator merely has to aspirate at least 10 ml of gastric juice from the stomach of the patient. When the level of the gastric juice inside the measurement container reaches the level sensor 19, the microprocessor deactivates the electric valve 1 and the pump 41, so that any further aspirated material is guided toward the suction duct and then toward the container for collecting the aspirated material R. After this, the microprocessor activates the agitator 21 and records the value detected by the pH probe 5; it then adds the ISA and, after 110 seconds of agitation, measures the value of the ammonia with the probe 6. Then, on the basis of the previously stored calibration parameters, the microprocessor calculates the value of pH and ammonium (in ppm) of the sample of gastric juice being tested and displays them on the specific displays of the card 56; it then compares these values with preset reference values and reports to the operator the results of the comparison, informing him as to the presence/absence of *H. pylori* infection and as to the acidity condition (normo-, hypo-achlorhydria) of the patient being tested, allowing to deduce in each instance the diagnostic procedure that is most suitable for the particular case. All this occurs in no more than 2 minutes, i.e., before the operator has ended the endoscopic test. During the testing procedure, no visual monitoring on the part of the operator is required; the reaching of the 10-ml level of suitably aspirated gastric juice, the acidity condition, the presence/absence of *H. pylori* and the diagnostic procedure to be followed are all reported verbally by the microprocessor 46 by way of the sound card 54 and the loudspeaker 57.

Analysis of the data and their reporting by way of voice messages is followed by the emptying of the measurement container 8, by its washing and then by the reintroduction of the solution. After this, the device is again ready for a new test (start button 50) or for shutdown (button 51). If the 10-ml level is not reached (due to insufficient availability of gastric juice in the stomach of the patient), the operator presses the start button 50 again. At this point, the microprocessor checks the level sensor 18, and if it finds it to be activated (i.e., there are at least 5 ml of juice), it conducts the test, warning the operator that the procedure is performed on a reduced sample. If instead the level indicator 18 is not activated (i.e., there are less than 5 ml of juice), the device warns the operator that the test cannot be performed and prepares itself for a new test.

When the operator has ended the session of tests, he presses the power-off button 51. The microprocessor 46 activates the suction of the solution, washes the measurement container 8, introduces therein the preservation solution, and switches off the machine M. The preservation solution can be constituted by one of the four liquids (suitably modified) used for calibration or by a mixture thereof (in relation to the type of pH and NH3 probe used).

During any step of the test, and even outside of said test, the operator can take advantage of the possibility to infuse water into the gastroscope or echoendoscope, in order to cleanse or fill the affected viscera. To do so, he merely has to press the pedal 53 that manages the water pump 40 and connect the water outlet duct to the instrument.

It has thus been shown that the invention achieves the intended aim and object.

The invention thus conceived is susceptible of numerous modifications and variations, all of which are within the scope of the appended claims.

All the details may further be replaced with other technically equivalent ones.

In the embodiments cited above, individual characteristics, given in relation to specific examples, may actually be interchanged with other different characteristics that exist in other embodiments.

Moreover, it is noted that anything found to be already known during the patenting process is understood not to be claimed and to be the subject of a disclaimer.

In practice, the materials used, as well as the shapes and dimensions, may be any according to requirements without thereby abandoning the scope of the protection of the appended claims.

The disclosures in Italian Patent Application No. BO2003A000091 from which this application claims priority are incorporated herein by reference.

What is claimed is:

1. A machine in combination with an endoscopic unit and a collection vessel, the machine having an inlet and an outlet, wherein the endoscopic unit has a suction duct, the suction duct being connected to the inlet of the machine, and wherein the collection vessel is connected to an exit of the machine and to a suction unit, the machine being able to identify presence/absence of *H. pylori* infection and acidity condition of a patient, the machine being constituted by:
    a measurement unit, the measurement unit being constituted by
    a container, the container being provided with means for aspirating gastric juices and an agitator for a mixture of gastric juice, water and reagents required for analysing the gastric juices, and
    at least a pH measurement probe and an ammonia measurement probe,
    a hydraulic section that comprises a set of tanks for the reagents and for the water,
    means for feeding said measurement unit, said means for feeding being connected to the tanks,
    a pump for feeding water into the stomach of the patient, the pump being connected the tanks
    an apparatus for controlling temperature of said container, and
    an electrical section, the electrical section comprising a programmable control unit, the programmable control unit being able to actuate and control said means for feeding the measurement unit and able to actuate and control said measurement unit, and comprising a microprocessor, wherein the microprocessor is configured to calculate pH and ammonium values of the aspired gastric juice based on measurements of the pH measurement probe and of the ammonia measurement probe, then to compare these pH and ammonium values with preset reference pH and ammonium values and to report verbally to an operator of the endoscope unit, within 2 minutes from the gastric juice aspiration, an acidity condition, a presence of *H. pylori* infection and a diagnostic procedure to be followed during endoscopy.

2. The machine according to claim 1, wherein said means for aspirating gastric juices comprise at least one pump.

3. The machine according to claim 1, wherein said means for feeding the measurement unit comprise at least one pump for sending said reagents and water and/or air.

4. The machine according to claim 1, wherein said apparatus for controlling the temperature of said container is a generator of heating air at an adjustable temperature.

5. The machine according to claim 1, wherein said container of said measurement unit is of a substantially closed type and is provided with connections for a plurality of ducts for a flow of liquids and/or air and for access of probes.

6. The machine according to claim 5, wherein said container is substantially cylindrical, said container comprising at least one temperature sensor and at least one level sensor suitable to indicate a presence of certain volumes of liquids within said container.

7. The machine according to claim 5, wherein said container comprises, on a side wall thereof, an emptying hole to which an intake is connected.

8. The machine according to claim 5, wherein said container contains at least one temperature sensor and a plurality of level sensors that are suitable to indicate a presence of certain volumes of liquids within the container.

9. The machine according to claim 1, wherein said agitator comprises
    a driving motor to a shaft of which a disk is rigidly coupled, said disk supporting a permanently magnetized bar, and
    an armature, which is also permanently magnetized and rests above the bottom of said container.

* * * * *